United States Patent
Trost et al.

(10) Patent No.: US 9,404,878 B2
(45) Date of Patent: Aug. 2, 2016

(54) SYSTEMS AND METHODS FOR DETECTING AN $H_2O_2$ LEVEL IN A COLD ASEPTIC FILLING SYSTEM THAT USES A PERACETIC ACID CLEANING SOLUTION

(75) Inventors: Detlef Trost, Kirchheimbolanden (DE); Holger Theyssen, Freinsheim (DE)

(73) Assignee: Diversey, Inc., Sturtevant, WI (US)

( * ) Notice: Subject to any disclaimer, the term of this patent is extended or adjusted under 35 U.S.C. 154(b) by 718 days.

(21) Appl. No.: 13/387,406

(22) PCT Filed: Jul. 26, 2010

(86) PCT No.: PCT/US2010/043213
§ 371 (c)(1),
(2), (4) Date: Mar. 12, 2012

(87) PCT Pub. No.: WO2011/017045
PCT Pub. Date: Feb. 10, 2011

(65) Prior Publication Data
US 2012/0161974 A1    Jun. 28, 2012

Related U.S. Application Data

(60) Provisional application No. 61/228,843, filed on Jul. 27, 2009.

(51) Int. Cl.
*G08B 21/00* (2006.01)
*G01N 27/06* (2006.01)

(52) U.S. Cl.
CPC ..................................... *G01N 27/06* (2013.01)

(58) Field of Classification Search
USPC .......................................................... 340/603
See application file for complete search history.

(56) References Cited

U.S. PATENT DOCUMENTS 4,229,299 A * 10/1980 Savitz ................. F04B 43/1215
   210/137
4,275,448 A *  6/1981 Le Dall ................ B01J 49/0095
   210/143

(Continued)

FOREIGN PATENT DOCUMENTS

JP       H60503162       4/1994
JP      2001183326 A     7/2001

(Continued)

OTHER PUBLICATIONS

International Search Report from International Patent Application PCT/US2010/043213, dated Feb. 23, 2011, 3 pages.

(Continued)

*Primary Examiner* — Naomi Small
(74) *Attorney, Agent, or Firm* — Michael Best & Friedrich LLP

(57) ABSTRACT

A system for detecting a hydrogen peroxide (H2O2) concentration in a cold aseptic filling system that uses a peracetic acid (PAA)-based cleaning solution is shown and described. The system includes a conductivity sensor configured to receive the PAA-based cleaning solution and to provide a signal representative of the electrical conductivity of the PAA-based cleaning solution. The system further includes a controller configured to receive the signal representative of the electrical conductivity of the PAA-based cleaning solution and to compare the signal to a threshold value associated with a setpoint H2O2 concentration.

15 Claims, 5 Drawing Sheets

(56) References Cited

U.S. PATENT DOCUMENTS

| | | | | |
|---|---|---|---|---|
| 4,680,271 | A | * | 7/1987 | Williams ............... G01N 21/78 422/3 |
| 4,848,381 | A | * | 7/1989 | Livingston ............... A23G 7/00 134/100.1 |
| 5,400,818 | A | * | 3/1995 | Cosentino ............. G01N 27/06 137/551 |
| 5,489,961 | A | * | 2/1996 | Burbury ................. G03D 3/065 396/570 |
| 5,503,720 | A | | 4/1996 | Teske |
| 5,745,039 | A | * | 4/1998 | Hof .......................... G01K 3/04 116/204 |
| 6,007,678 | A | * | 12/1999 | Linsten ................ D21C 9/1042 162/65 |
| 6,156,267 | A | * | 12/2000 | Pai ............................ A61L 2/24 422/116 |
| 6,189,368 | B1 | | 2/2001 | Ichida et al. |
| 6,318,151 | B1 | | 11/2001 | Wang et al. |
| 6,387,238 | B1 | * | 5/2002 | Merk ..................... A01N 37/16 204/252 |
| 6,558,529 | B1 | | 5/2003 | McVey |
| 6,656,423 | B1 | * | 12/2003 | Joslyn ....................... A61L 2/04 210/175 |
| 2002/0119574 | A1 | * | 8/2002 | Berg ........................ A01J 7/022 436/55 |
| 2005/0186116 | A1 | | 8/2005 | Centanni |
| 2006/0283808 | A1 | * | 12/2006 | Kadlec ...................... C02F 1/76 210/746 |
| 2008/0011884 | A1 | * | 1/2008 | Ueda .................... B08B 9/0813 239/561 |
| 2008/0210262 | A1 | * | 9/2008 | Lauzon ................... A47J 31/60 134/22.12 |
| 2008/0307353 | A1 | * | 12/2008 | Molducci .............. G06F 3/0482 715/802 |
| 2010/0304494 | A1 | * | 12/2010 | Tokhtuev ............ B01L 3/50273 436/100 |

FOREIGN PATENT DOCUMENTS

| | | |
|---|---|---|
| JP | 2004313780 | 11/2004 |
| JP | 2009113858 A | 5/2009 |

OTHER PUBLICATIONS

Japanese Office Action for Japanese Application No. 2012-522929 dated Jan. 7, 2014 (2 pages).
Office Action from the Japanese Patent and Trademark Office for Application No. 2012-522929 dated Aug. 12, 2014 (11 pages).
Australian Patent Examination Report No. 1 for application No. 2010281539 dated Aug. 20, 2013 (2 pages).

* cited by examiner

SYSTEMS AND METHODS FOR DETECTING AN $H_2O_2$ LEVEL IN A COLD ASEPTIC FILLING SYSTEM THAT USES A PERACETIC ACID CLEANING SOLUTION

BACKGROUND OF THE INVENTION

The present invention relates generally to the field of cold aseptic filling (e.g., CAF, aseptic cold filling, ACF, aseptic filling, etc.).

In cold aseptic filling systems, food, drink, or drug containers are sterilized with a cleaning solution before they are filled. Heat is not used for the sterilization. After cleaning solution is used, it is often recovered (e.g., into a recovery tank) and reused for sterilizing future batches of containers.

As a cleaning solution containing peracetic acid (PAA) and hydrogen peroxide ($H_2O_2$) is reclaimed and reused, the PAA concentration drops relative to the $H_2O_2$. Accordingly, in cold aseptic filling systems using such a cleaning solution, systems or processes are sometimes set up to add fresh PAA-based cleaning solution to the cold aseptic filling loop to maintain a desired PAA concentration in the solution to be sprayed on or into the containers. This addition results in increasing $H_2O_2$ levels. High $H_2O_2$ levels can result in undesirable corrosion of container surfaces or equipment surfaces, non-compliance with food processing regulations, or other undesirable issues.

Conventional systems and methods for detecting an $H_2O_2$ level in a cold aseptic filling system using a PAA-based cleaning solution include robotic or automatic titration or manual titration of liquid in the reclamation tank.

SUMMARY OF THE INVENTION

One embodiment of the invention relates to a system for detecting a hydrogen peroxide ($H_2O_2$) concentration in a cold aseptic filling system that uses a peracetic acid (PAA)-based cleaning solution. The system includes a conductivity sensor configured to receive the PAA-based cleaning solution and to provide a signal representative of the electrical conductivity of the PAA-based cleaning solution. The system further includes a controller configured to receive the signal representative of the electrical conductivity of the PAA-based cleaning solution and to compare the signal to a threshold value associated with a setpoint $H_2O_2$ concentration.

Another embodiment of the invention relates to a method for detecting a hydrogen peroxide ($H_2O_2$) concentration in a cold aseptic filling system. The method includes providing a peracetic acid (PAA)-based cleaning solution circulating through the cold aseptic filling system to a conductivity sensor. The method further includes measuring the electrical conductivity of the PAA-based cleaning solution with the conductivity sensor. The method yet further includes providing a signal representative of the measured electrical conductivity from the conductivity sensor to a controller. The method also includes using the controller to compare the signal representative of the electrical conductivity of the PAA-based cleaning solution to a threshold value associated with a setpoint $H_2O_2$ concentration.

Another embodiment of the invention relates to a controller for detecting a hydrogen peroxide ($H_2O_2$) level in an aseptic filling system that uses a peracetic acid (PAA)-based cleaning solution. The controller includes a processing circuit configured to receive a signal representative of the electrical conductivity of the PAA-based cleaning solution and to compare the signal to a threshold value associated with a setpoint $H_2O_2$ level. The processing circuit is configured to at least one of: (a) cause a display coupled to the processing circuit to display indicia representative of the electrical conductivity of the PAA-based cleaning solution, and (b) generate an alarm when the signal representative of the electrical conductivity of the PAA solution is greater than the threshold value associated with the setpoint $H_2O_2$.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Before turning to the figures which illustrate the exemplary embodiments in detail, it should be understood that the disclosure is not limited to the details or methodology set forth in the description or illustrated in the figures. It should also be understood that the terminology is for the purpose of description only and should not be regarded as limiting.

Referring generally to the Figures, a system for detecting an $H_2O_2$ level in a cold aseptic filling system that uses a PAA-based cleaning solution is shown and described. The system includes a conductivity sensor that receives the PAA-based cleaning solution. The output from the conductivity sensor is compared to a threshold value associated with a setpoint $H_2O_2$ level to detect whether the $H_2O_2$ level is undesirable or should otherwise be acted upon (e.g., displayed, provided to personnel with an alarm, used in an automation process, etc.).

Figure 1A:
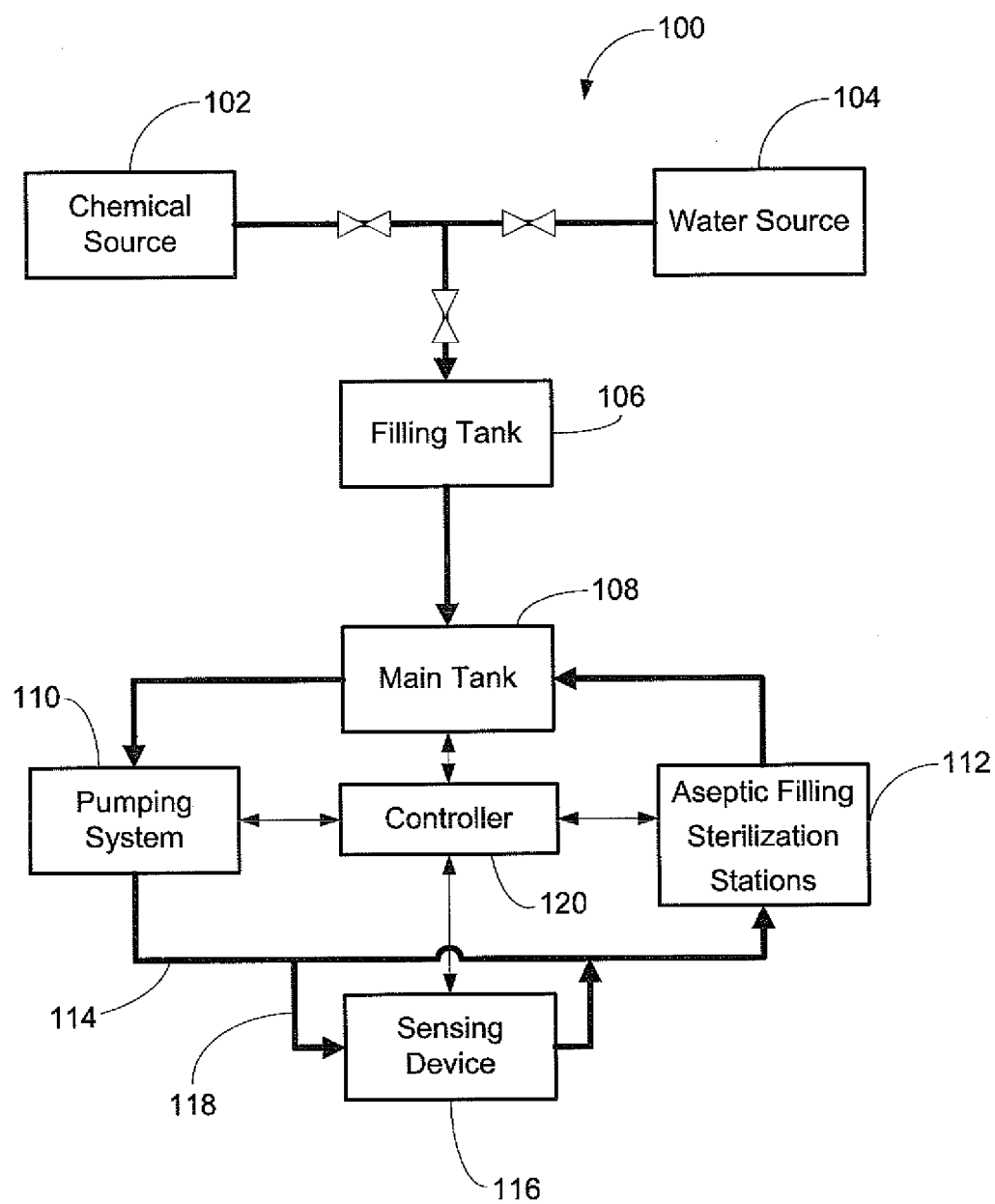
FIG. 1A is a block diagram of a system for detecting an $H_2O_2$ level in a cold aseptic filling system that uses a PAA-based cleaning solution, according to an exemplary embodiment.

Referring now to FIG. 1A, a simplified hydraulics diagram of a cold aseptic filling system 100 is illustrated, according to an exemplary embodiment. Cold aseptic filling system 100 generally operates by providing a cleaning solution through piping 114 (e.g., conduit, tubing, etc.) to one or more cold aseptic filling sterilization stations 112 to sterilize containers or other objects. At cold aseptic filling sterilization stations 112, the cleaning solution is provided to containers or other target objects (e.g., medical devices, contaminant sensitive electronics, etc.) for sterilization. For example, the cleaning solution may be sprayed on, sprayed in, or otherwise caused to fill or cover the target objects. Run-off or other remainder of cleaning solution from cold aseptic filling sterilization stations 112 is reclaimed (i.e., collected) and recirculated through piping 114.

Referring still to FIG. 1A, in an exemplary embodiment the cleaning solution utilized in the system is a PAA-based cleaning solution, the chemicals of which are provided to the system via chemical source 102 and mixed with water from water source 104 to provide a PAA-based cleaning solution of the desired concentration. Chemical source 102 and water source 104 may be tanks and pump-based systems, inlets for allowing human personnel to add chemicals, or otherwise. As shown, the flow of fluid from chemical source 102 and/or water source 104 may be controlled or metered with one or more valves (e.g., electronically controlled valves, etc.). Fluid from chemical source 102 may mix, settle, and/or be stored in filling tank 106 until provided to main tank 108 for circulation through the loop including cold aseptic filling sterilization stations 112. According to the embodiment shown in FIG. 1, main tank 108 can be used for mixing reclaimed cleaning solution with new doses of chemicals and/or water from sources 102, 104. Controller 120 or another control system may be used to control such dosing or mixing.

Pumping system 110 draws cleaning solution from main tank 108 and pumps the cleaning solution through piping 114. Pumping system 110 may be a variable speed system controlled in whole or in part by controller 120 or another control circuit. As shown in FIG. 1, bypass piping 118 is configured to provide cleaning solution to sensing device 116 in parallel with piping provided to cold aseptic filling sterilization stations 112. Accordingly, sensing device 116 can easily be activated and when sensing device 116 is active, it can continuously be measuring parameters of the cleaning solution provided to cold aseptic filling sterilization stations 112. In an exemplary embodiment, fluid provided to sensing device 116 is added back to the fluid circuit or loop which provides the cleaning solution to cold aseptic filling sterilization stations 112. In some embodiments controller 120 may coordinate activities among pumping system 110, cold aseptic filling sterilization stations 112, sensing device 116, and/or main tank 108.

Figure 1B:
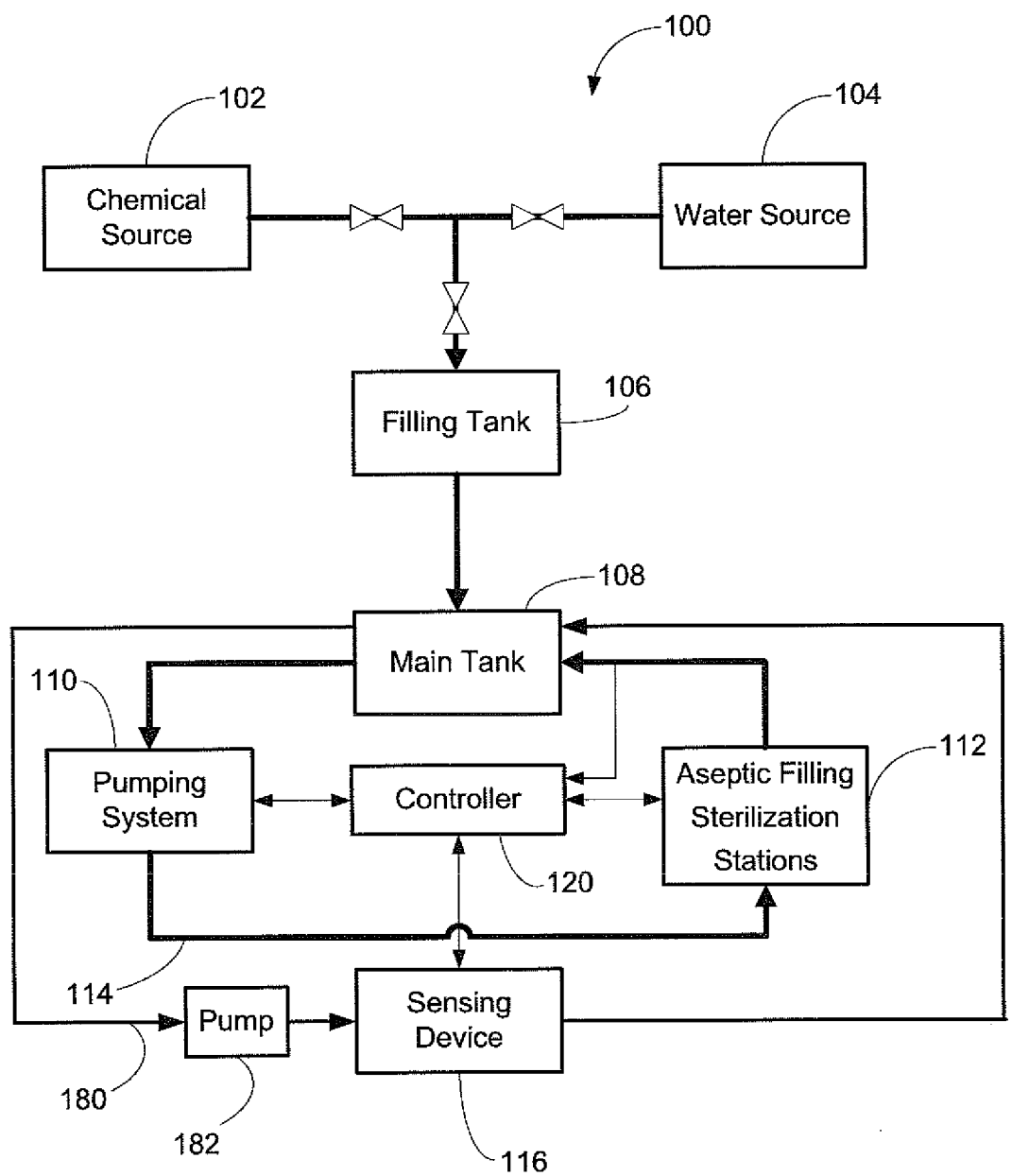
FIG. 1B is a block diagram of another system for detecting an $H_2O_2$ level in a cold aseptic filling system that uses a PAA-based cleaning solution, according to another exemplary embodiment.

Referring briefly to FIG. 1B, an alternative to FIG. 1A for integrating sensing device 116 into cold aseptic filling system 100 is shown. Particularly, the sensing device shown in FIG. 1B is provided the PAA-based cleaning solution via fluid piping 180 which is in parallel with but separate from piping 114. Pump 182 (which may be controlled by controller 120, a controller of sensing device 116, or otherwise) is configured to pump PAA-based cleaning solution from main tank 108 through sensing device 116. Referring to both FIG. 1A and FIG. 1B, while one sensing device is shown and described, it should be appreciated that multiple sensing devices may be provided for different purposes. For example, a Bi-Ox measuring device sold by JohnsonDiversey GmbH & Co. may be provided in addition to sensing device 116 to measure PAA concentration of the cleaning solution, flow, or another value not measured by sensing device 116. In other embodiments, the conductivity sensing aspects of sensing device 116 described herein may be incorporated into the Bi-Ox device.

The systems and methods described herein relate to cold aseptic filling systems through which a PAA-based cleaning solution is pumped. In some embodiments of this disclosure, "PAA-based cleaning solution" can mean any solution that uses PAA as a sterilizer. In other embodiments PAA-based cleaning solution can mean a solution that contains a concentration of PAA as well as a concentration of $H_2O_2$. In an exemplary embodiment, the PAA-based cleaning solution contains about fifteen percent PAA and twenty percent $H_2O_2$ prior to being mixed with or diluted by water. In other embodiments, different concentration levels may be targeted by different users or control systems of system 100 (e.g., to obtain an optimal mix of sterilization capability, cost, and/or corrosive qualities). It should be noted that while the target (e.g., setpoint) concentration balance may be obtained or approximately obtained when the system is first started (e.g., when filling tank 106 or main tank 108 are first filled), over time the concentrations can become askew due to the reclaiming and recirculating of some of the cleaning solution that occurs.

For example, as the peracetic acid (PAA) and hydrogen peroxide ($H_2O_2$) solution is reclaimed and reused, the PAA concentration level may drop relative to the $H_2O_2$ concentration. In other embodiments the PAA concentration level may be maintained within a desired concentration range but the $H_2O_2$ may rise to undesired or unacceptable concentration levels. In some systems fresh PAA solution may be dosed (e.g., added, injected, mixed with, etc.) to the recirculating cleaning solution over time to seek a setpoint PAA concentration. Such dosing of fresh PAA may result in an undesirable increase of $H_2O_2$ levels over time. Because high $H_2O_2$ levels can result in undesirable corrosion of filling equipment, non-compliance with food processing regulations, or the like, a system such as that shown in FIG. 1A or FIG. 1B may conduct a partial or total exchange of the PAA-based cleaning solution in the system when $H_2O_2$ concentration levels are increased beyond an established setpoint, threshold or maximum value. As stated above, conventional systems and methods for detecting an $H_2O_2$ level in a cold aseptic filling system using a PAA acid solution include robotic or automatic titration or manual titration of liquid in the reclamation tank to determine when to conduct the total or partial exchange of fluid in the system. In contrast to the conventional titration processes, Applicants' solution advantageously places sensing device 116 such that it (e.g., in combination with a controller or controllers) may monitor $H_2O_2$ concentration levels by sensing the electrical conductivity of the PAA-based cleaning solution. Accordingly, with reference to FIGS. 1A-B, sensing device 116 includes a conductivity sensor configured to receive the PAA-based cleaning solution of the cold aseptic filling system and to provide a signal (e.g., analog, digital) representative of the electrical conductivity of the PAA-based cleaning solution. The conductivity sensor can provide the signal to a controller local to sensing device 116 or a remotely located controller (e.g., controller 120). The controller is configured to receive the signal representative of the electrical conductivity of the PAA-based cleaning solution and to compare the signal to a threshold value associated with a setpoint $H_2O_2$ concentration. Sensing device 116 is shown and described in greater detail in subsequent Figures.

Figure 2:
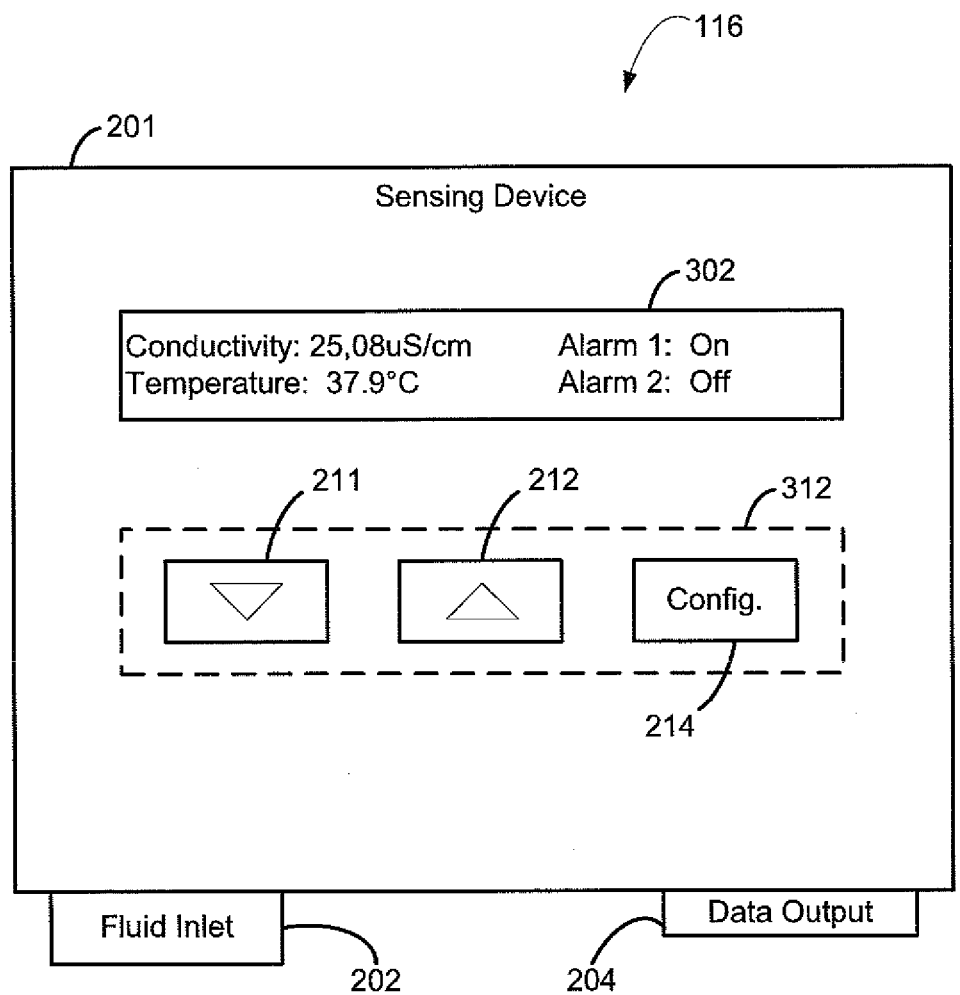
FIG. 2 is simplified plan view of a sensing device for use with FIG. 1A or 1B, according to an exemplary embodiment.

Referring now to FIG. 2, a simplified top-down plan view of sensing device 116 of FIGS. 1A and 1B is shown, according to an exemplary embodiment. Sensing device 116 is shown as having a generally rectangular-shaped housing 201 but could be of any shape or size according to various embodiments. Sensing device 116 is shown to include a display 302 (e.g., LCD display, OLED display, dot matrix display, etc.) and user interface (UI) elements 312. Display 302, as shown, may be configured to display indicia of the conductivity of liquid in contact with the sensor, temperature of the liquid, whether a first or second alarm is active, or otherwise. UI elements 312 (e.g., buttons 211, 212) may be used to cycle through different views of data, change values during calibration or configuration, or to otherwise interact with sensing device 116. UI elements 312 (e.g., button 214) may be used to cause the device to enter a configuration or calibration mode or to "save" configuration or calibration settings once they are changed with buttons 211, 212.

Figure 3:
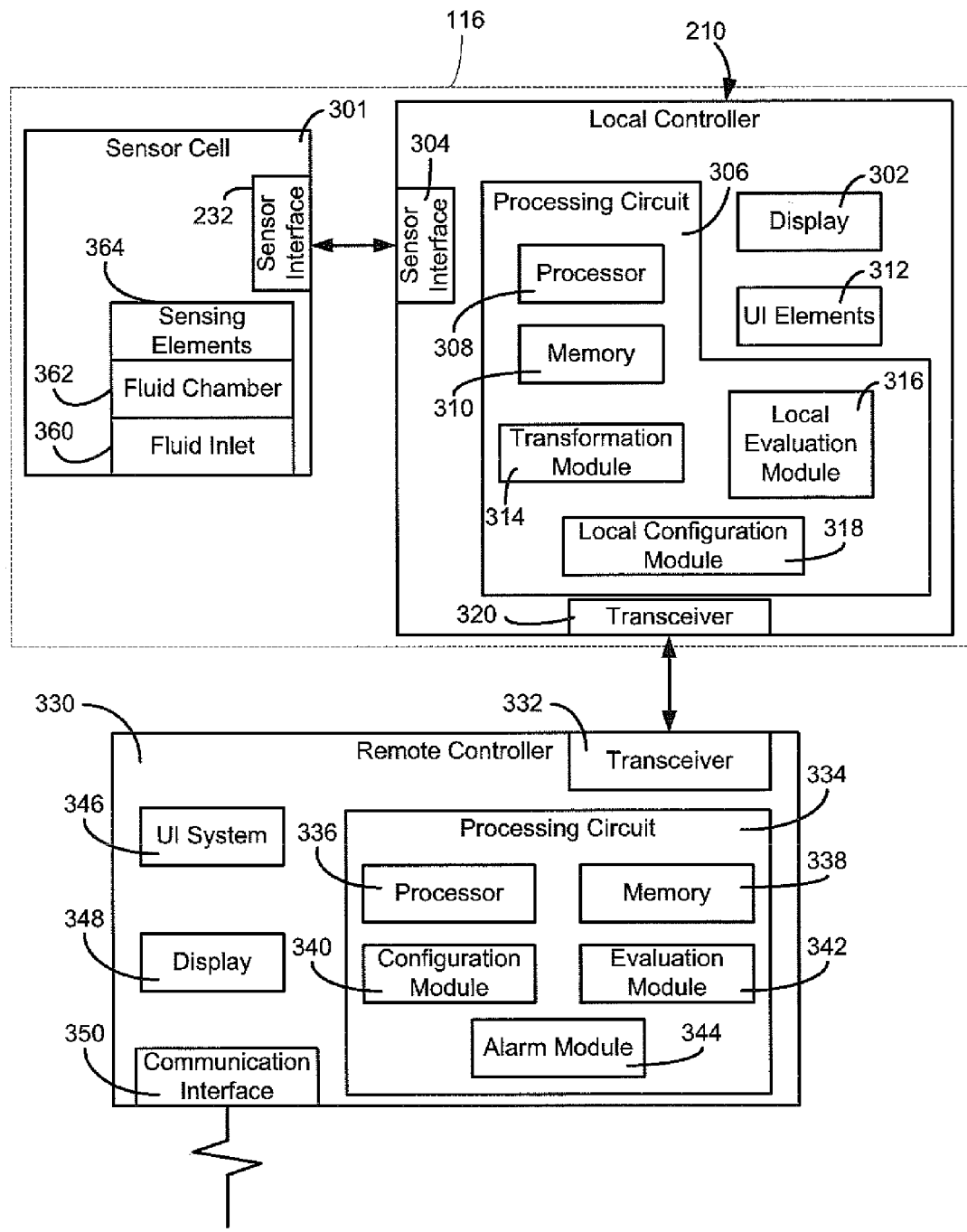
FIG. 3 is a block diagram of a sensing device (e.g., of previous Figures) in communication with a remote controller, according to various exemplary embodiments.

Cleaning solution from piping 118 in FIG. 1A or piping 180 in FIG. 1B may be pumped into sensing device 116 via a fluid inlet 360 (shown in FIG. 3). Fluid inlet 360 may place the cleaning solution in contact with one or more sensing elements (e.g., electrodes, temperature sensors, sensing membranes, etc.). Data may be output from sensing device 116 via data output 204 which may correspond to a jack or other terminal of transceiver 320 shown in FIG. 3.

Referring now to FIG. 3, a block diagram of sensing device 116 which is shown to include sensor cell 301 and local controller 210 is shown, according to an exemplary embodiment. As in the embodiment shown in FIG. 2, sensing device 116 may be one physical device (e.g., where housing 201 contains both sensor cell 301 and local controller 210). In other embodiments, "sensing device" 116 may include a sensor cell 301 that is wired to local controller 210 (e.g., via sensor interface pair 232, 304) but not contained within the same housing. Sensing device 116 may be a Condutec type conductivity sensor sold by Hengesbach GmbH & Co. KG. For example, FIG. 2 may illustrate Hengesbach's "compact unit" version of the Condutec conductivity sensor where the sensor cell is joined to its controller via a rigid housing. FIG. 3 may illustrate Hengesbach's "split unit" version where sensor cell 301 is wired to local controller 210 but is not otherwise physically coupled thereto. It should be noted that any suitable device suitable for measuring the conductivity of PAA-based cleaning solutions may be used in place of a Hengesbach conductivity sensor.

Referring further to FIG. 3, sensor cell 301 (whether integrated with local controller 210 or separate from local controller 210) is shown to include a fluid inlet 360, a fluid chamber 362, and sensing elements 364. As shown in FIG. 3, sensor cell 301 may include only one fluid input or output. In other embodiments, sensor cell 301 may include multiple inputs or outputs. Fluid chamber 362 (regardless of the input/output configuration) may be configured to receive fluid and to provide the fluid to sensing elements 364. Sensing elements 364 may include a power source, electrodes, sensing circuitry, or other sensing devices configured to determine the conductivity of liquid in fluid chamber 362.

Referring further to FIG. 3, remote controller 330 is shown, according to various exemplary embodiments. In the embodiment shown in FIG. 3, sensor cell 301 is configured to provide a signal representative of the conductivity of the PAA-based cleaning solution to local controller 210. Local controller 210 is configured to conduct one, more or zero processing steps on the signal prior to forwarding the signal (transformed or not) to remote controller 330. Remote controller 330 may be a relatively central or head controller such as controller 120 shown in FIG. 1 or may be another controller in or outside of the cold aseptic filling system. Remote controller 330 may be configured to conduct any number of processing, storage, and/or aggregation activities with the signals it receives. For example, local controller 210 may be configured to receive the signal representative of the conductivity of the PAA-based cleaning solution and to compare the signal to a threshold value associated with a setpoint $H_2O_2$ concentration.

Sensor cell 301 is shown as having a sensor interface 232 to which a wire (e.g., conductive cabling, optical cabling, etc.) is attached. Sensor interface 232, as previously noted, may be analog or digital. Further, sensor interface 232 may include a standard jack or terminal or include a proprietary or custom jack, terminal, solder point, or other interface. On local controller 210, sensor interface 304 may be of the same or a different type than sensor interface 232. Sensor interface 304, for example, may include receiving circuitry configured to receive, smooth, convert analog to digital, or otherwise handle signals from sensor cell 301.

In an exemplary embodiment, signals received from sensor cell 301 are transformed into an industry standard output by processing circuit 306. In other exemplary embodiments, processing circuit 306 is configured to convert signals from sensor cell 301 into a proprietary format compatible with a proprietary receiver or logic of a remote controller. Processing circuit 306 may be or include one or more circuit boards, analog circuits, integrated circuits, digital circuits, or the like configured to provide the logic or input and output (I/O) activities described in the present application. Processing circuit 306 is shown to include processor 308 and memory 310. Processor 308 may be or include an integrated circuit, a general purpose processor, a field programmable gate array (FPGA), a programmable logic controller (PLC), a combination thereof, or otherwise and configured to complete and/or facilitate the activities of a controller described herein (e.g., as variously shown and described in and with reference to FIGS. 4A and 4B).

Local controller 210 is further shown to include memory 310 which may be configured to store historical data received at sensor interface 304, calibration information or configuration information, serve as temporary storage while signals from sensor cell 301 are processed, and/or store computer code for execution by processor 308. When executed, such computer code (e.g., stored in memory 310 or otherwise, script code, object code, etc.) configures processing circuit 306, processor 308 or more generally local controller 210 for the activities described herein. In various exemplary embodiments, processing circuit 306 is configured to receive signals from sensor interface 304 and to prepare and send the signals to remote controller 330 in a controlled fashion—such preparation and I/O activities may be controlled by processing circuit 306 once it has been configured with computer code stored in memory 310. Similarly, modules 314-318 may be or include computer code, analog circuitry, one or more integrated circuits or another collection of logic circuitry configured to complete or cause local controller 210 to complete the activities for each module described below.

As also shown in previous Figures, local controller 210 includes a display 302 and user interface (UI) elements 312. Display 302 may be a liquid crystal display (LCD) or another suitable display type capable of displaying words, symbols, graphics, or other indicia. Display 302 may also or alternatively include one or more lights such as LEDs that can indicate, for example, operational faults, status signals, or the like without being displayed as text or a more complex symbol. UI elements 312 may be or include one or more buttons, touch pads, scrolling devices, keyboards, or the like configured to allow user-interaction with local controller 210. In an exemplary embodiment, output from sensor cell 301 may be calibrated by a user via local controller 210. For example, when sensing device 116 is first inserted into a cold aseptic filling system and/or a fresh PAA-based cleaning solution of the desired concentration is circulated through the cold aseptic filling system, a user may enter one or more calibration parameters to the controller via UI elements 312. As a part of a calibration process, processing circuit 306 may cause one or more initial readings to be displayed via display 302 or otherwise assist the user in the calibration process. Input received at UI elements 312 and/or other calibration or setup related activities may be controlled by processing circuit 306 via local configuration module 318. Local configuration module 318, for example, may be configured to prompt the user (e.g., via display 302) for target concentration values, tested conductivity values, tested concentration values, setpoint values, or otherwise use this information with actual input from sensor cell 301 to "zero" or otherwise calibrate local controller 210 for handling signals from sensor cell 301. Local configuration module 318 may be configured to save in memory or otherwise set parameters for operation based on its calibration activity. For example, local configuration module 318 may be configured to store one or more values or offsets in memory 310 that local controller can use to transform signals from sensor cell 301 into a calibrated and standardized (or otherwise expected) format for sending to remote controller 330. Transformation module 314 may be configured to utilize the values or offsets determined during calibration or otherwise to conduct the transformation of the signals. For example, transformation module 314 may use a calibration value to boost, trim, modulate, re-clock, step-up, step-down or otherwise adjust the voltage (e.g., millivolts) to characteristics expected by remote controller 330.

Referring further to FIG. 3, local evaluation module 316 may be a part of local controller 210. Local evaluation module 316 may be configured to, for example, conduct the actual interpretation of the signals from sensor cell 301 rather than or in addition to remote controller 330. For example, local evaluation module 316 may be configured to compare the signal representative of conductivity from sensor cell 301 to a threshold value associated with a setpoint $H_2O_2$ concentration for the PAA-based solution received by sensor cell 301. In other embodiments, local evaluation module 316 is configured to convert the signal from sensor cell 301 into a conductivity value (e.g., in units of microsiemens per centimeter (pS/cm)). Local evaluation module 316 may use the conductivity value and a pre-stored/pre-configured relationship or equation (e.g., linear, non-linear, etc.) to determine an $H_2O_2$ concentration of the PAA-based cleaning solution. In such embodiments, processing circuit 306 and/or evaluation module 316 may be configured to provide indicia of the conductivity or $H_2O_2$ concentration to display 302, another device via transceiver 320, or otherwise output the indicia. When the displayed indicia relates to the $H_2O_2$ of the PAA-based cleaning solution, the indicia may be $H_2O_2$ concentration in terms of percentage, $H_2O_2$ concentration in terms of parts per million, or otherwise. Local evaluation module 316 may also or alternatively be configured to display a warning (e.g., flashing light, warning code, explanatory text, etc.) when the $H_2O_2$ concentration level μs greater than a setpoint (e.g., maximum) $H_2O_2$ concentration. In some embodiments, the logic of local evaluation module 316 that detects whether the $H_2O_2$ concentration is too high or above a setpoint may not actually calculate or convert conductivity to concentration. For example, local evaluation module 316 may compare the conductivity reading from sensor cell 301 to a conductivity pre-determined to correspond with an undesirable $H_2O_2$ concentration and use such comparison (without more calculation) to output, for example, that $H_2O_2$ of the PAA-solution is too high. Such a pre-determined relationship between the conductivity output from sensor cell 301 and a threshold associated with a setpoint $H_2O_2$ concentration may be input into local controller 210 after determination via an automatic or manual testing or calibration procedure.

While in some embodiments the activities of the above paragraph and local evaluation module 316 may be conducted entirely by local controller 210, in other embodiments remote controller 330 conducts such activities via its processing circuit 334 and/or evaluation module 342. Similarly, configuration module 340 may have the features of local controller 210's configuration module 318. In other embodiments, both local controller 210 and remote controller 330 may be configured to allow a user to conduct appropriate calibration, setup, or configuration activities via modules 314, 340. Processor 336 and/or memory 338 of remote controller 330 may be similar to processor 308 or memory 310 of local controller 210 or otherwise. In an exemplary embodiment, local controller 210 has a simplified processing circuit 306 or processor 308 relative to remote controller 330. For example, remote controller 330 may be configured for many other control tasks relating to the cold aseptic filling system (such as controller 120). Remote controller 330 may be, for example, a full-featured computer.

Local controller 210 provides signals (e.g., analog outputs, digital outputs, etc.) representative of the conductivity of the PAA-based cleaning solution to remote controller 330 via transceiver 320. While transceiver 320 may include a transmitter and receiver pair, in other embodiments remote controller 330 may use a transmitter to provide the information to remote controller 330. For the purposes of this application, the terms transmitter and transceiver are used interchangeably for devices that are able to at least output signals of the type and content relevant to the present disclosure. Communication interface 350 of remote controller 330 may be configured to communicate the results of its processing and/or signals received from sensor cell 301 or local controller 210 to a network or further control system. For example, in addition to or instead of the activities of local evaluation module 316, evaluation module 342 may be configured to use connected network devices to initiate a process to empty and refill the cold aseptic filling system with new PAA-based cleaning solution when the conductivity of the PAA-based cleaning solution is greater than a threshold value associated with the setpoint $H_2O_2$ concentration.

Processing circuit 334 is further shown to include alarm module 344 which may be configured to generate an alarm (e.g., for display 348, an audible alarm for output by an audio system, an alarm message for transmitting to another device (PDA, cellphone, laptop, etc.) via communication interface 350, etc.) when evaluation module 342 determines that the signal representative of the conductivity of the PAA-based cleaning solution is greater than the threshold value associated with the setpoint $H_2O_2$. Evaluation module 342 may also or alternatively be configured to cause display 348 to show indicia (e.g., graphics, text, symbols, etc.) representative of the conductivity of the PAA-based cleaning solution. In yet other embodiments, evaluation module 342 may be configured to cause a determined $H_2O_2$ level to be displayed via display 348.

Figure 4A:
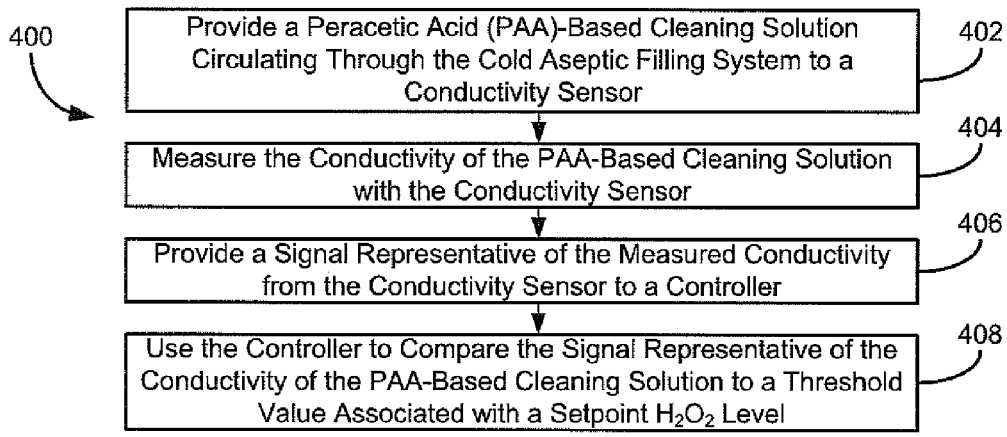
FIG. 4A is a flow chart of a process for detecting a hydrogen peroxide ($H_2O_2$) level in a cold aseptic filling system, according to an exemplary embodiment.

Referring now to FIG. 4A, a flow chart of a process 400 for detecting a hydrogen peroxide ($H_2O_2$) level in a cold aseptic filling system is shown, according to an exemplary embodiment. Process 400 is shown to include providing a peracetic acid (PAA)-based cleaning solution circulating through the cold aseptic filling system to a conductivity sensor (step 402). Process 400 is further shown to include measuring the electrical conductivity of the PAA-based cleaning solution with the conductivity sensor (step 404). Process 400 further includes providing a signal representative of the measured electrical conductivity from the conductivity sensor to a controller (step 406). Process 400 further includes using the controller to compare the signal representative of the conductivity of the PAA-based cleaning solution to a threshold value associated with a setpoint $H_2O_2$ level (step 408). In various exemplary embodiments, the controller that conducts step 408 may be controller 120, controller 210, remote controller 330, or any other controller associated with the cold aseptic filling system.

Figure 4B:
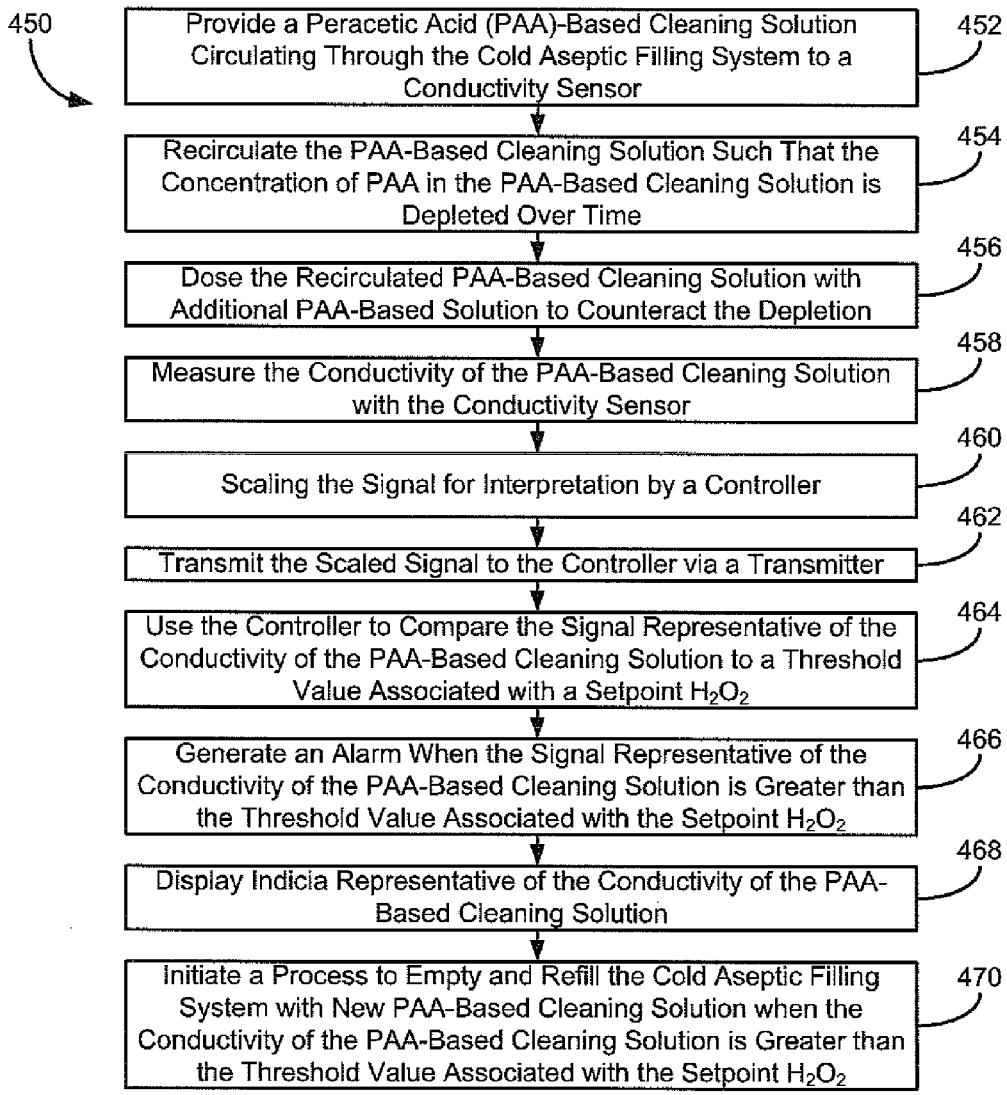
FIG. 4B is a more detailed flow chart of another process for detecting a hydrogen peroxide ($H_2O_2$) level in a cold aseptic filling system, according to an exemplary embodiment.

Referring now to FIG. 4B, a more detailed flow chart of a process 450 for detecting a $H_2O_2$ level in a cold aseptic filling system is shown, according to an exemplary embodiment. Process 450 is shown to include providing (e.g., exposing) a peracetic acid (PAA)-based cleaning solution circulating through the cold aseptic filling system to a conductivity sensor (step 452). Process 450 further includes recirculating the PAA-based cleaning solution (step 454)(e.g., in a cold aseptic filling system such as that described above that reclaims used solution). The solution may be recirculated such that the concentration of PAA in the PAA-based cleaning solution is depleted over time. Process 450 further includes dosing (e.g., supplementing, injecting, adding to, etc.) the recirculated PAA-based cleaning solution with additional PAA-based cleaning solution to counteract the depletion (step 456). Controller 120 may automatically control or meter such dosing.

Process 450 further includes measuring the electrical conductivity of the PAA-based cleaning solution with the conductivity sensor (step 458). The measurement of conductivity may be completed via any number of suitable techniques for measuring conductivity including, for example: providing a voltage from one electrode through a first electrode through the PAA-based cleaning solution to a second electrode, measuring the current in the circuit formed by the electrodes and the solution, determining resistance using the measured current and the known voltage, and determining the reciprocal of the resistance. All of these measuring activities may be conducted by components of, for example, sensor cell 301 or some may be completed by, for example, sensor cell 301 in concert with controller 210 and/or controller 330.

Process 450 further includes providing a signal to a circuit local to the conductivity sensor (e.g., local controller 210 and its processing circuit 306) that scales the signal for interpretation by a controller (step 460) and transmitting the scaled signal to the controller (e.g., remote controller 330, controller 120) via a transmitter (step 462). Process 450 further includes using the controller to compare the signal representative of the conductivity of the PAA-based cleaning solution to a threshold value associated with a setpoint $H_2O_2$ (step 464). When the signal representative of the conductivity of the PAA-based cleaning solution is greater than the threshold value associated with the setpoint $H_2O_2$, the controller generates an alarm (step 466). Process 450 further includes displaying indicia representative of the conductivity of the PAA-based cleaning solution (step 468). In alternative embodiments a determined $H_2O_2$ level may be displayed.

Process 450 further includes initiating a process to empty and refill the cold aseptic filling system with new PAA-based cleaning solution when the conductivity of the PAA-based cleaning solution is greater than the threshold value associated with the setpoint $H_2O_2$ (step 470). In other words, the controller may include logic or may provide a signal to another controller that includes logic for using the determination regarding $H_2O_2$ concentration to automate the refreshing of a cold aseptic filling system when $H_2O_2$ is too high. For example, the controller may: discontinue operation of the cold aseptic filling sterilization stations, open a valve in tanks (e.g., tanks 106, 108) to drain solution in the system, flush the system with water or another fluid or gas, and refill the system with proper amounts of chemical and/or water to restart the cold aseptic filling concentration levels.

The present disclosure contemplates methods, systems and program products on any machine-readable media for accomplishing various operations. The embodiments of the present disclosure may be implemented using existing integrated circuits, computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A system for detecting a hydrogen peroxide ($H_2O_2$) concentration in a cold aseptic filling system that uses a peracetic acid (PAA)-based cleaning solution, the system comprising:

a primary conduit through which the PAA-based cleaning solution is circulated;

a bypass conduit fluidly coupled to the primary conduit;

a conductivity sensor positioned in the bypass conduit, the conductivity sensor configured to receive a portion of the PAA-based cleaning solution from the primary conduit via the bypass conduit and to provide a signal representative of the electrical conductivity of the PAA-based cleaning solution and to compare the signal to a threshold value associated with a setpoint $H_2O_2$ concentration, wherein the concentration of PAA in the PAA-based cleaning solution is depleted over time, wherein the cold aseptic filling system is configured to dose the PAA-based cleaning solution with additional PAA to counteract the depletion, and wherein the portion of the PAA-based cleaning solution provided to the conductivity sensor is returned to the primary conduit.

2. The system of claim 1, wherein the cold aseptic filling system is configured to recirculate the PAA-based cleaning solution.

3. The system of claim 1, wherein the controller is configured to generate an alarm when the signal representative of the electrical conductivity of the PAA-based cleaning solution is greater than the threshold value associated with the setpoint $H_2O_2$ concentration.

4. The system of claim 1, wherein the controller is remote from the conductivity sensor and the system further comprises:
a transmitter locally coupled to the conductivity sensor, the transmitter configured to receive the signal representative of the electrical conductivity of the PAA-based cleaning solution and to provide the signal to the controller.

5. The system of claim 4, further comprising:
a display coupled to the transmitter and configured to display indicia representative of the electrical conductivity of the PAA-based cleaning solution.

6. The system of claim 4, wherein the transmitter is configured to wirelessly transmit the signal via radio frequency communications.

7. The system of claim 1, wherein the controller includes a processing circuit configured to receive the signal representative of the electrical conductivity of the PAA-based cleaning solution, wherein the processing circuit is configured to cause a display coupled to the processing circuit to display indicia representative of the electrical conductivity of the PAA-based cleaning solution.

8. The controller of claim 7, wherein the processing circuit is further configured to generate an alarm when the signal representative of the electrical conductivity of the PAA-based cleaning solution is greater than the threshold value associated with the setpoint $H_2O_2$ concentration.

9. A method for detecting a hydrogen peroxide ($H_2O_2$) concentration in a cold aseptic filling system, the method comprising:
circulating a peracetic acid (PAA)-based cleaning solution through a primary conduit of the cold aseptic filling system;
bypassing a portion of the PAA-based cleaning solution to a conductivity sensor;
measuring the electrical conductivity of the PAA-based cleaning solution with the conductivity sensor;
providing a signal representative of the measured electrical conductivity from the conductivity sensor to a controller;
using the controller to compare the signal representative of the electrical conductivity of the PAA-based cleaning solution to a threshold value associated with a setpoint $H_2O_2$ concentration;
routing the portion of the PAA-based cleaning solution back to the primary conduit; recirculating the PAA-based cleaning solution such that the concentration of PAA in the PAA-based cleaning solution is depleted over time; and
dosing the recirculated PAA-based cleaning solution with additional PAA to counteract the depletion.

10. The method of claim 9, further comprising:
generating an alarm when the signal representative of the electrical conductivity of the PAA-based cleaning solution is greater than the threshold value associated with the setpoint $H_2O_2$ concentration.

11. The method of claim 9, further comprising:
initiating a process to empty and refill the cold aseptic filling system with new PAA-based cleaning solution when the electrical conductivity of the PAA-based cleaning solution is greater than the threshold value associated with the setpoint $H_2O_2$.

12. The method of claim 9, wherein providing a signal representative of the measured electrical conductivity from the conductivity sensor to a controller comprises:
providing the signal to a circuit local to the conductivity sensor that scales the signal for interpretation by the controller; and
transmitting the scaled signal to the controller via a transmitter.

13. The method of claim 9, further comprising:
displaying indicia representative of the electrical conductivity of the PAA-based cleaning solution.

14. A method for detecting a hydrogen peroxide ($H_2O_2$) concentration in a cold aseptic filling system, the method comprising:
circulating a peracetic acid (PAA)-based cleaning solution through the cold aseptic filling system to a conductivity sensor;
measuring the electrical conductivity of the PAA-based cleaning solution with the conductivity sensor;
providing a signal representative of the measured electrical conductivity from the conductivity sensor to a controller; and
using the controller to compare the signal representative of the electrical conductivity of the PAA-based cleaning solution to a threshold value associated with a setpoint $H_2O_2$ concentration;
wherein the conductivity sensor is in parallel with hydraulics of the cold aseptic filling system such that the conductivity sensor continuously receives a flow of the PAA-based cleaning solution when the cold aseptic filling system is active with fluid flow, and
wherein the flow of PAA-based cleaning solution received by the conductivity sensor is directed back into fluid flow circulating through the cold aseptic filling system.

15. The method of claim 9, wherein the threshold conductivity value is associated with a setpoint $H_2O_2$ concentration of more than 7500 parts per million.

* * * * *